United States Patent [19]
Brochier et al.

[11] Patent Number: 5,458,647
[45] Date of Patent: Oct. 17, 1995

[54] FINGER JOINT PROSTHESIS FOR METACARPOPHALANGEAL AND INTERPHALANGEAL JOINTS

[75] Inventors: Michel Brochier, Haute Jarrie; Jacques Gaidry, Eybens; Claude Moreau, Saint Nizier; Francçois Moutet, Meylan; René Ranc, Grenoble, all of France

[73] Assignee: Commissariat a l'Energie Atomique, Paris, France

[21] Appl. No.: 204,238

[22] PCT Filed: Sep. 6, 1991

[86] PCT No.: PCT/FR92/00845

§ 371 Date: Apr. 26, 1994

§ 102(e) Date: Apr. 26, 1994

[87] PCT Pub. No.: WO93/04644

PCT Pub. Date: Mar. 18, 1993

[30] Foreign Application Priority Data

Sep. 6, 1991 [FR] France .................. 91 11043

[51] Int. Cl.[6] ........................... A61F 2/42
[52] U.S. Cl. ............... 623/21; 623/18; 403/157
[58] Field of Search ............... 623/18, 20, 21, 623/50, 52; 403/158, 157, 150, 119

[56] References Cited

U.S. PATENT DOCUMENTS

| 3,813,700 | 6/1974 | Tavernetti et al. . |
| 4,034,946 | 7/1977 | Zimmer, Jr. ............... 248/183 |
| 4,655,778 | 4/1987 | Koeneman ............... 623/21 |
| 5,154,382 | 10/1992 | Hoshino ............... 248/185 |

FOREIGN PATENT DOCUMENTS

| 0055406 | 7/1982 | European Pat. Off. . |
| 0214773 | 3/1987 | European Pat. Off. . |
| 2455205 | 12/1980 | France ............... 403/157 |
| 2566272 | 6/1984 | France . |
| 2590794 | 12/1985 | France . |
| 1328497 | 8/1973 | United Kingdom . |
| 2015882 | 3/1978 | United Kingdom . |
| 2015881 | 9/1979 | United Kingdom . |
| 9011739 | 10/1990 | WIPO . |
| 9304644 | 3/1993 | WIPO . |

*Primary Examiner*—David Isabella
*Assistant Examiner*—Laura Fossum
*Attorney, Agent, or Firm*—Pearne, Gordon, McCoy & Granger

[57] ABSTRACT

A finger joint prosthesis for metacarpalphalangeal and interphalangeal joints is provided including two diaphyseal parts which are implantable in the phalangeal and/or metacarpal bones and are fixed to a pivotable joint. The joint includes a female cap, a male cap, a shaft force fitted into two openings in the female cap and extending through an opening in the male cap, and a collar surrounding the shaft in the male cap. The joint also includes two side flanges which hold disks for holding the collar in place. The female and male caps and the side flanges are made of titanium alloy while the collar, the shaft, and the disks are made of pyrocarbon so that friction during rotation of the joint occurs only between components that are made of pyrocarbon.

2 Claims, 2 Drawing Sheets

FINGER JOINT PROSTHESIS FOR METACARPOPHALANGEAL AND INTERPHALANGEAL JOINTS

BACKGROUND OF THE INVENTION

The present invention relates to the field of finger joint prostheses used for replacing phalangeal and metacarpophalangeal joints.

Various diseases, such as post-traumatic arthrosis, evolutive polyarthritis, infectious arthritis and certain rheumatic states lead to a progressive deterioration or destruction of the finger joints. Thus, for a number of years, joint implants or prostheses of various types have been developed in the surgical field in order to attempt to restore the use of the fingers of the hand in patients suffering from such diseases.

The destruction of metacarpophalangeal (MP) and proximal interphalangeal (IPP) joints of the long fingers leads to a therapeutic problem for the hand surgeon which has not yet been completely solved PELLEGRINI V. D., BURTON R. I., Osteoarthritis of the proximal interphalangeal joint of the hand, arthroplasty or fusion, J. Hand Surg. 1990, 15-A,2, 194–209). The recovery of functional amplitudes requires the replacement of joint surfaces, no matter whether the joint destruction is the consequence of a post-traumatic arthrosis, the development of an evolutive polyarthritis or an infectious arthritis.

Details will be given of the main solutions envisaged and applied up to now, while on each occasion indicating their disadvantages.

The appearance of silicone implants SWANSON A. B. Silicone rubber implants for replacement of arthritic or destroyed joints in the hand, Surg. Clin. North Am., 1968, 48, 1113–1127), has been subject to certain advances in this field. However, over a period of time numerous complications inherent in the material have appeared such as the fracture of implants, lateral instabilities, lack of strength, residual pain, etc. The reaction to silicone foreign bodies, which is a possible source of autoimmune pathology makes the use thereof arbitrary particularly in the case of young patients EKFORS O. ARO H. MAKI J. AHO A. J. Cystic osteolysis induced by silicone rubber prosthesis. Arch. Pathol. Lab. Med. 1984, 108, 225–227).

The unsatisfactory results with such implants, particularly in post-traumatic cases, have led to research being carried out on other arthroplastic solutions BLAIR W. F., SHURR D. G., BUCKWALTER J. A. Metacarpophalangeal joint arthroplasty with a metallic hinged prosthesis. Clin. Orthop. 1984, 184, 156–163, and CONDAMINE J. L., BENOIT J. Y., COMTET J. J., AUBRIOT J. (in French) Proposal for digital arthroplasty: critical study of the initial results, Ann. Chir. Main, 1988,7,4, 282–297).

Two arthroplasty concepts are possible, namely stressed arthroplasties on the one hand, where the two articulated parts are mechanically joined and semi and non-stressed on the other, where the two parts have no mechanical link.

The problems of lateral stability encountered with non or semi-stressed prostheses have led the applicant to opt for a stressed hinged implant consequently only having a single degree of freedom, namely that of bending-extension.

This hinged implant type raises two problems, namely that of the strength and the reliability of the actual hinge and that of the anchoring of the diaphysed parts, no matter whether or not they are sealed.

Existing arthroplasties are produced from stainless steel and polyethylene or titanium and polyethylene, besides silicone.

As a further illustration of the state of the art reference can be made to FR-A-2 590 794, FR-A-2 605 878 and FR-A-2 620 932. These three documents disclose the use of diaphysed parts or pins for fixing in the medullary channel of the finger bones. The part issue at their common end onto a swivel joint and/or rotation system having one or two degrees of freedom and make it possible to reconstitute a freedom of finger movement which is as close as possible to that given by natural joints.

SUMMARY OF THE INVENTION

The present invention specifically relates to a finger joint prosthesis for metacarpophalangeal or interphalangeal joints making it possible to overcome the aforementioned prior art difficulties by combining in an originally designed hinge the materials constituted by titanium and its alloys on the one hand and pyrolytic carbon on the other.

This finger joint prosthesis, implantable in finger bones, is characterized in that it comprises a female cap joined to the first diaphysed part which is provided with two aligned openings transverse with respect to the first part. A male cap is provided with a transverse opening with respect to the second diaphysed part and cooperates with the female cap. The male cap is integral with the second diaphysed part. A shaft is force fitted into the two openings of the female cap and extends through the opening of the male cap. A collar surrounds the shaft and is force fitted in the opening of the male cap. Two lateral flanges are each provided with a square cutout and end lugs insertable into notches of the female cap. The cutouts serve to receive disks for holding in place the collar. The collar emerges on either side of the opening of the male cap, and the thickness of each disk exceeds that of the lateral flanges.

In a preferred embodiment, the male and female caps, as well as the lateral flanges are made from a titanium alloy, while the collar, the shaft and the disks are made from pyrocarbon, so that the friction during the rotation of the joint takes place solely between the pyrocarbon parts.

The field of potential applications for the joint prosthesis according to the invention is very wide and more particularly relates to all cases of definitive joint destruction of MP and IPP-type joints, no matter what the origin thereof.

The actual hinge of the prosthesis is constituted by two medullary parts made from titanium alloy (TA6V) joined by a pyrocarbon shaft, which rotates freely in a pyrocarbon bearing. The pyrocarbon is obtained in the deposit state on a compatible substrate (generally graphite) by the thermal decomposition of a gaseous hydrocarbon. The joint shaft is produced according to this procedure by coating a graphite cylinder. According to the invention, the prosthesis structure makes it possible to avoid any contact or friction other than pyrocarbon on pyrocarbon. The low friction coefficient and the high resistance to wear of such a pair, which has been proved on a test bench for the particular structure, associated with the universally recognized biocompatibility of the pyrocarbon lead to an excellent reliability and a very good tolerance with respect to the prosthesis. Titanium guarantees the rigidity and robustness of the medullary pins. Its biocompatibility and mechanical qualities are well known. A pair of materials of a very robust and time-reliable nature is consequently combined in the case of titanium and pyrocarbon.

The thus produced hinge has a displacement of 120° in both extension and bending. If necessary, e.g. lowering the tonus of the bending apparatus, it is possible to create a break to the passive extension of the hinge by putting into place a mini-abutment.

Finally, the fixing of the medullary pins takes place by means of methyl methacrylate in order to permit an active mobilization without immediate post-operative phase limitation.

The invention is described in greater detail hereinafter relative to an embodiment of a finger joint prosthesis described in non-limitative manner with reference to the attached FIGS. 1 and 2, wherein show:

DETAILED DESCRIPTION OF THE PREFERRED EMBODIMENTS

Figure 1:
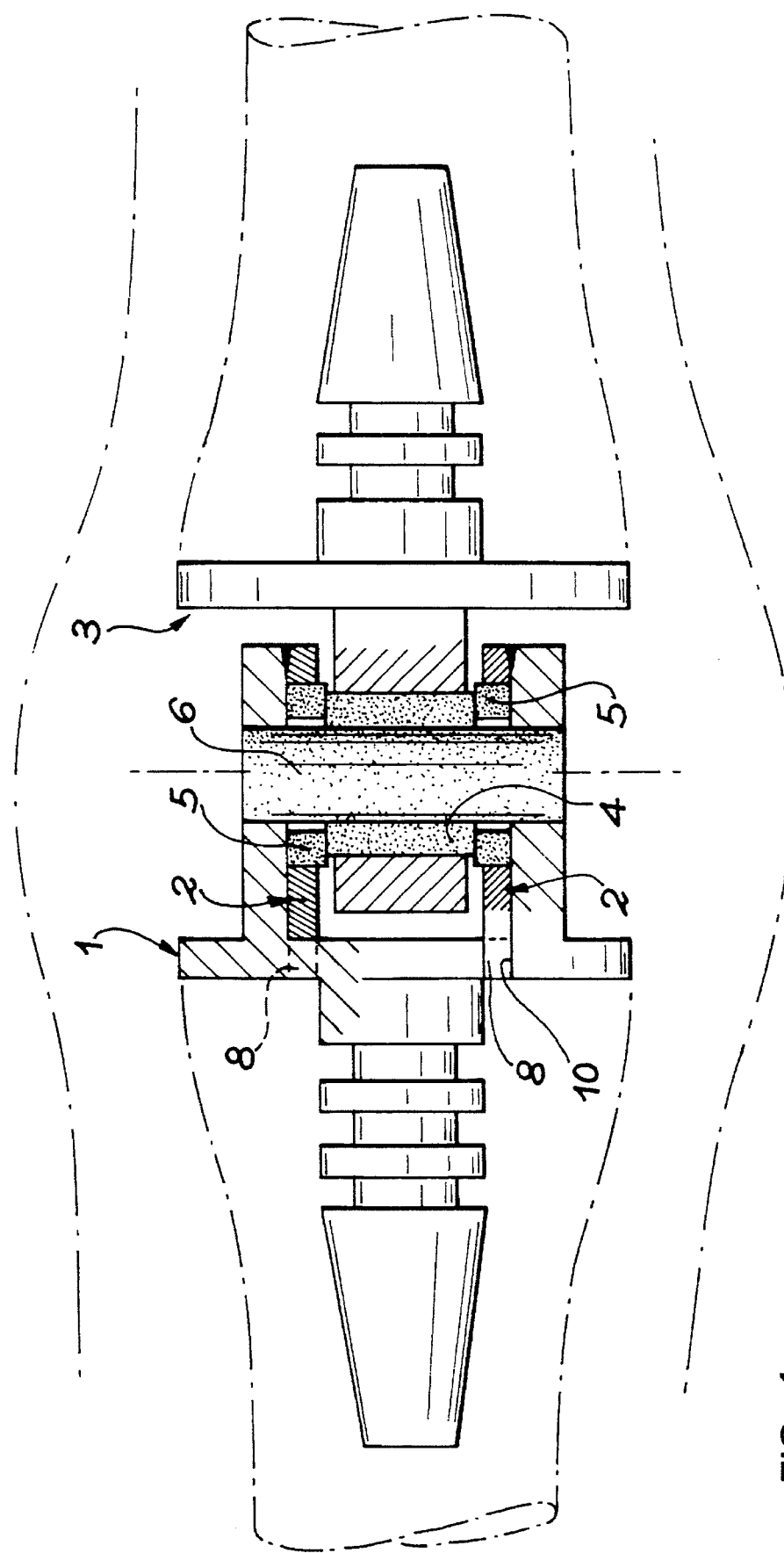
FIG. 1 A cross-sectional view of a finger joint prosthesis according to the invention.

FIG. 1 shows the two diaphysed parts 1 and 3 provided in conventional manner with grooves for facilitating their fixing in the medullary canal of the phalangeal or metacarpeal bones into which they are introduced. The diaphysed part or pin 1 is terminated at its end located on the side of the joint by a female cap having two aligned openings transverse with respect to the axis of the pin. The latter details can be more easily gathered from the exploded view of FIG. 2. The diaphysed part 3, opposite to the part 1, is terminated by a male cap, which is also more clearly visible in FIG. 2 and which will be described hereinafter. This male cap is provided with a transverse opening with respect to the diaphysed part 3 and which serves to cooperate with the female cap of the diaphysed part 1. A shaft 6 is force fitted into the two openings of the female cap and gently slides in the collar 4 force fitted into the opening of the male cap. It forms the pivot pin of the prosthesis. A collar 4 surrounds the shaft 6 and is engaged in the opening of the male cap, thus serving as a housing for the shaft 6.

Figure 2:
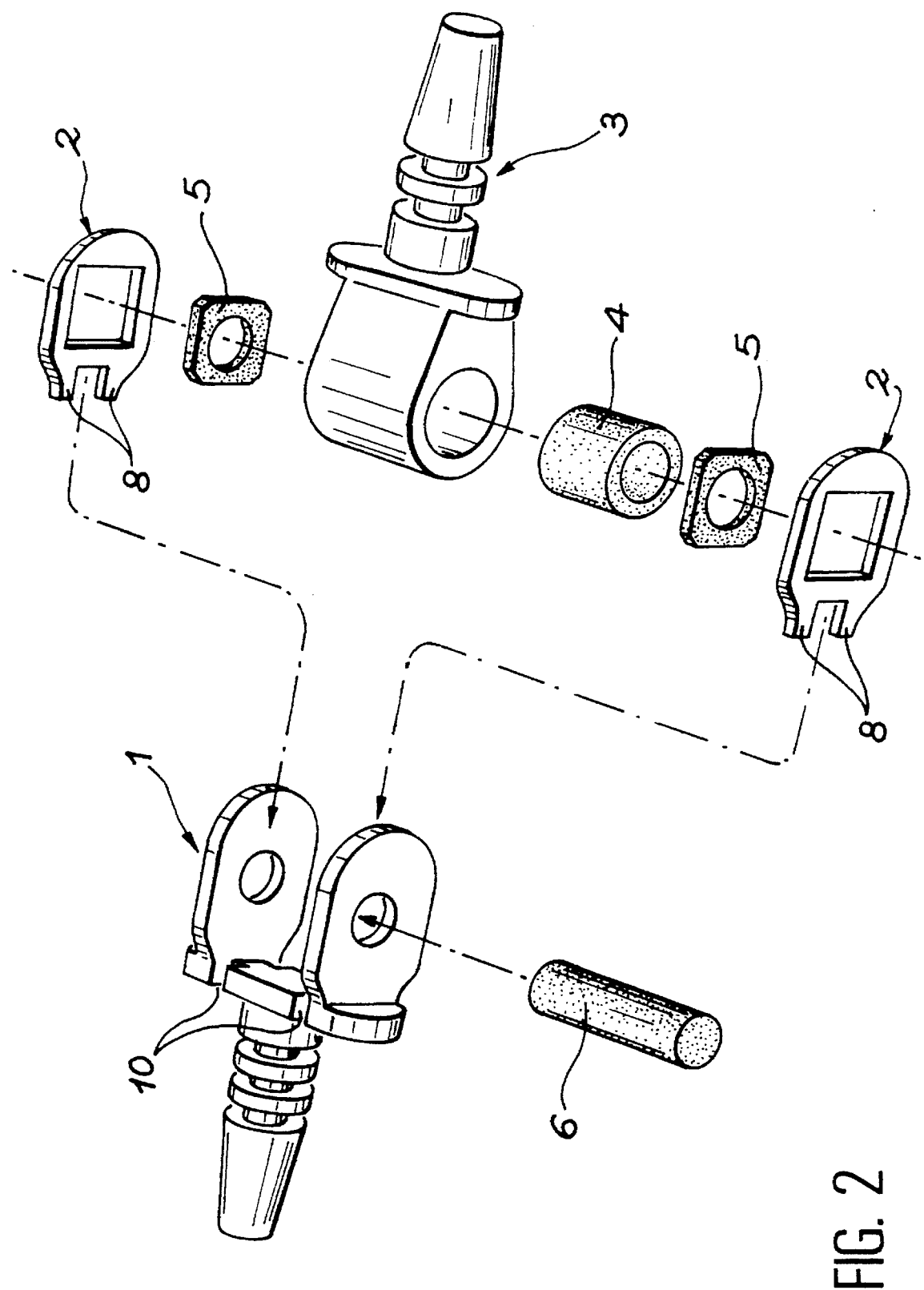
FIG. 2 An exploded view of the different components of this joint prosthesis.

According to the invention, two lateral flanges 2, which can also be more easily seen in FIG. 2, are provided with a square cutout and end lugs for insertion in notches of the female cap. The cutouts of the lateral flanges 2 are intended to receive disks 5 for holding in place the collar 4.

As has been explained hereinbefore, the male 3 and female 1 caps, as well as the lateral flanges 2 are made from titanium alloy and in preferred and more specific manner from the alloy TA6V. The collar 4, the disks 5 and the shaft 6 are made from pyrocarbon as a result of the friction resistance properties thereof. Moreover, and this constitutes an important feature of the invention, the collar 4 which is fixed in the opening of the portion of the male cap 3 has a length slightly greater than that of the the opening, so as to emerge on either side thereof. In addition, and this is a second important feature of the structure of the prosthesis according to the invention, the thickness of the disks 5 exceeds that of the lateral flanges 2 in which they are inserted. The two above conditions in combination then lead to the essential result of the invention, according to which during the rotation of the joint, the only parts which are in contact and which therefore develop friction with respect to one another are pyrocarbon parts and excludes any titanium alloy part. Thus, the disks 5 come into contact with the collar 4 and the latter is mounted in rotary manner about the shaft 6. Therefore, the robustness and long-life of the joint prosthesis according to the invention are completely guaranteed.

FIG. 2 shows the components of the pivoting joint prosthesis in dismantled form making it more easily possible to see the exact shapes of each part, the openings of the female 1 and male 3 caps, as well as those of the lateral flanges 2, whose square central opening is intended to contain the square profile of the lateral disks 5. The collar 4 and the shaft 6 have respective dimensions permitting them to be fitted into one another, the assembly then being fitted and fixed by force engagement of the shaft 6 in the openings of the female cap 1. It is also possible to see on the lateral flanges 2 the end lugs 8 making it possible to fix them in notches 10 provided for this purpose at the base of each female cap 1.

At the end of fitting, it may be advantageous to make a weld spot, e.g. with a laser in order to definitively join the lateral flanges 2 and the female cap 1.

A wear-resistance test on the joint prosthesis according to the invention was carried out on a test machine simulating the movement of the finger in bending-extension with an angular displacement of 120° and a speed of two cycles per second. Prostheses which underwent this test and were then dismantled and examined revealed no trace of wear observable with a binocular magnifier with a magnification of 50 after 20 million cycles.

Finally, the invention is not limited to the use of pyrocarbon for the collar 4, the disks 5 and the shaft 6. Biocompatible materials having a low friction coefficient can also be used.

In the same way, titanium or one of its alloys can be replaced by any other biocompatible material having adequate mechanical properties for use in a joint prosthesis according to the invention.

We claim:

1. Finger joint prosthesis for metacarpophalangeal and interphalangeal joints having first and second diaphysed parts (1, 3) implantable in phalangeal and metacarpeal bones, each of the diaphysed parts being integral with a pivoting joint and having a longitudinal axis, said finger joint prosthesis comprising:

a female cap (1) joined to the first diaphysed part (1) provided with two aligned openings transverse with respect to the longitudinal axis of the first diaphysed part;

a male cap (3) provided with a transverse opening with respect to the longitudinal axis of the second diaphysed part and cooperating with the female cap, said male cap being integral with the second diaphysed part;

a shaft (6) force fitted into the two openings of the female cap (1) and extending through the opening of the male cap (3);

a collar (4) surrounding the shaft and force fitted in the opening of the male cap (3), said collar emerging from each side of said opening of said male cap; and two lateral flanges (2) each provided with a square aperture and end lugs (8) insertable in notches (10) of the female cap, said apertures serving to receive disks (5) for holding in place the collar, said disks (5) having a thickness exceeding a thickness of the lateral flanges (2).

2. Joint prothesis according to claim 1, wherein said male (3) and cap, said female (1) cap and said lateral flanges (2) are made from titanium alloy and the collar (4), the shaft (6) and the disks (5) are made from pyrocarbon, so that friction taking place during rotation of the joint only occurs between the pyrocarbon parts.

* * * * *

UNITED STATES PATENT AND TRADEMARK OFFICE
CERTIFICATE OF CORRECTION

PATENT NO. : 5,458,647
DATED : October 17, 1995
INVENTOR(S) : Brochier et al.

It is certified that error appears in the above-indentified patent and that said Letters Patent is hereby corrected as shown below:

On the face of the patent, section [75], line 3, delete "Francçois" and insert --François--.

Column 1, line 22, before "PELLEGRINI" insert --(--;

line 33, before "SWANSON" insert --(--;

line 43, before "EKFORS" insert --(--;

line 48, before "BLAIR" insert --(--; and line 65, after "hinge" insert --,-- (comma).

Column 3, after line 9, insert the centered heading --BRIEF DESCRIPTION OF THE DRAWINGS--; and line 15, delete the centered heading "BRIEF DESCRIPTION OF THE DRAWINGS".

Column 5, line 2, delete "and" (first occurrence).

Signed and Sealed this

Nineteenth Day of March, 1996

BRUCE LEHMAN

*Attest:*

*Attesting Officer*  *Commissioner of Patents and Trademarks*